United States Patent
Algawi et al.

(10) Patent No.: US 10,660,742 B2
(45) Date of Patent: May 26, 2020

(54) EXPANDABLE BREAST IMPLANT (71) Applicant: Biosense Webster (Israel) Ltd., Yokneam (IL)

(72) Inventors: Yehuda Algawi, Binyamina (IL); Assaf Govari, Haifa (IL); Ilya Sitnitsky, Nahariya (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 75 days.

(21) Appl. No.: 15/983,035

(22) Filed: May 17, 2018

(65) Prior Publication Data
US 2019/0350697 A1 Nov. 21, 2019

(51) Int. Cl.
*A61F 2/12* (2006.01)
*G16H 40/67* (2018.01)
*A61L 27/02* (2006.01)
*A61L 27/18* (2006.01)

(52) U.S. Cl.
CPC .............. *A61F 2/12* (2013.01); *A61L 27/025* (2013.01); *A61L 27/18* (2013.01); *G16H 40/67* (2018.01); *A61F 2230/0026* (2013.01); *A61F 2250/0002* (2013.01); *A61F 2250/0003* (2013.01); *A61F 2250/0096* (2013.01)

(58) Field of Classification Search
CPC ....................................................... A61F 2/12
USPC ......................................................... 623/7–8
See application file for complete search history.

(56) References Cited

U.S. PATENT DOCUMENTS

| 5,571,178 | A | * | 11/1996 | Ledergerber | A61F 2/12 623/8 |
| 6,228,116 | B1 | * | 5/2001 | Ledergerber | A61F 2/0077 623/8 |
| 2006/0069403 | A1 | * | 3/2006 | Shalon | A61F 2/12 606/192 |
| 2010/0010531 | A1 | * | 1/2010 | Shalon | A61F 2/12 606/192 |

(Continued)

FOREIGN PATENT DOCUMENTS

| EP | 2958492 A1 | 12/2015 |
| WO | 2014/130863 A1 | 8/2014 |

OTHER PUBLICATIONS

Extended European Search Report dated Jul. 26, 2019 for the European Patent Application No. 19174906.8.

*Primary Examiner* — Suzette J Gherbi
(74) *Attorney, Agent, or Firm* — Volpe and Koenig, P.C.

(57) ABSTRACT

An expandable breast implant eliminates the need for multiple procedures and injections and is also capable of self-administered or automatic expansion that is safe in any environment. The expandable breast implant design includes an upper matrix, a lower matrix, and a middle layer. The upper matrix comprises a plurality of cells containing a first reagent. The lower matrix comprises a plurality of wells containing a second reagent. The middle layer acts as a barrier between the upper matrix and the lower matrix. The middle layer may be activated and controlled to form openings. The first reagent from the cells in the upper matrix mixes with the second reagent from the wells in the lower matrix through the selected openings in the middle layer. The reagents react to form a gas that permeates through a hydrophobic membrane into an expandable shell to enlarge the breast implant.

20 Claims, 14 Drawing Sheets

(56) References Cited

U.S. PATENT DOCUMENTS

2015/0351900 A1* 12/2015 Glicksman ............. A61B 90/94
          623/8
2017/0333179 A1* 11/2017 Forsell ....................... A61F 2/12
2018/0256276 A1*  9/2018 Zamarripa ............. A61B 90/02
2018/0325700 A1* 11/2018 Selter ........................ A61F 2/12
2019/0038397 A1*  2/2019 Becker ...................... A61F 2/12
2019/0223971 A1*  7/2019 Payne .................... A61B 90/02
2019/0290382 A1*  9/2019 Martinez ............... A61B 90/02

* cited by examiner

EXPANDABLE BREAST IMPLANT

SUMMARY

Current breast implant procedures involve a complicated series of major and minor medical procedures, which are a source of pain and inconvenience for the patient. In the first major medical procedure, a physician makes an incision in the patient and inserts a tissue expander to create space between the skin and the muscle. Thereafter, a series of minor medical procedures are required to expand the tissue expander to the desired size. This procedure is done through multiple saline injections performed by a physician every few weeks. In addition to the inconvenience of multiple physician visits, the saline injections involve a long, painful, and uncomfortable process for the patient. After the tissue expander has been expanded to the desired size, a second major medical procedure is performed to remove the expander and insert a permanent breast implant into the space created by the tissue expander.

There have been developments in expandable breast implants to reduce the number of procedures and physician visits. For example, some devices used pressurized carbon dioxide cartridges, which were susceptible to failure at high elevations. With such implants, a patient could not travel by air for an extended period of time. Accordingly, these implants were not an optimal solution.

It would therefore be desirable to have an expandable breast implant that eliminates the need for multiple medical procedures and injections. It would also be desirable to have an expandable breast implant capable of self-administered expansion that is safe and convenient.

There is provided, according to the described embodiments, a medical apparatus including an expandable breast implant that eliminates the need for multiple procedures and injections, with the capability for self-administered expansion that is safe in any environment. The expandable breast implant includes an upper matrix, a lower matrix, and a middle layer that separates the upper matrix and lower matrix. The upper matrix is covered by a hydrophobic membrane. The upper matrix comprises a plurality of cells containing a first reagent. The lower matrix comprises a plurality of wells containing a second reagent. The middle layer acts as a barrier between the upper matrix and the lower matrix. The middle layer may be activated and controlled to form openings at selected locations. The first reagent from the cells in the upper matrix mixes with the second reagent from the wells in the lower matrix through the selected openings in the middle layer. The reagents react to generate a gas, which is released through the hydrophobic membrane top of the upper matrix. The gas permeates the hydrophobic membrane into an expandable shell to enlarge the breast implant.

BRIEF DESCRIPTION OF THE DRAWINGS

The present embodiments are illustrated by way of example, and not by way of limitation, in the figures of the accompanying drawings in which.

DETAILED DESCRIPTION OF THE EMBODIMENTS

Various embodiments are described in the following paragraphs. Where like elements have been depicted in multiple embodiments, identical or similar reference numerals have been used for ease of understanding.

Figure 1:
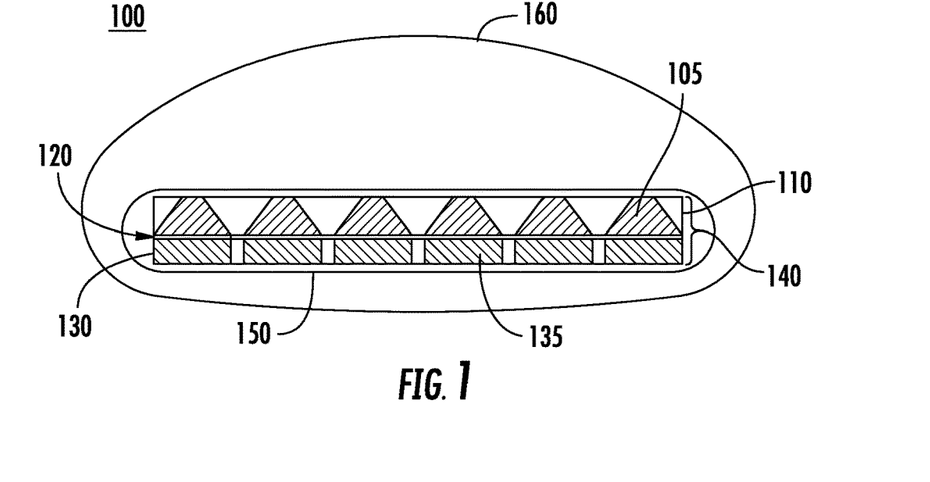
FIG. 1 is an example cross-sectional view of a multi-layer design for an expandable breast implant.

FIG. 1 is an example cross-sectional view of a multi-layer expandable breast implant 100. The expandable breast implant 100 includes an expandable shell 160, an upper matrix 110, a lower matrix 130, and a middle layer 120. In one embodiment, the expandable shell 160 may comprise silicone, and the shell 160 is filled with one or more different types of silicone. In other embodiments, the shell may be filled with saline or another material, or even unfilled.

The upper matrix 110 comprises a plurality of cells 105. As shown in FIG. 1, the cells 105 may be angularly shaped with the cell 105 gradually increasing in size toward the middle layer 120. Each cell 105 contains a first reagent. The lower matrix 130 comprises a plurality of wells 135. Each well 135 is aligned with a complimentary cell 105. The wells 135 contain a second reagent. The middle layer 120 forms a barrier between the upper matrix 110 and lower matrix 130. The upper matrix 110, lower matrix 130, and middle layer 120 may be coupled together with glue, heat-sealing, or any other appropriate manner to form the multi-layer structure 140. The multi-layer structure 140 may be encased in a hydrophobic membrane 150, such that gases permeate the hydrophobic membrane 150 while liquid is denied passage. In one alternative embodiment, the hydrophobic membrane 150 covers only the top of the upper matrix 110. In this embodiment the hydrophobic membrane 150 may be coupled to the top of the upper matrix 110 via any appropriate manner such as glue, heat-sealing, or the like. The multi-layer structure 140 and the hydrophobic membrane 150 are further encased in an expandable shell 160 to form the expandable breast implant 100. In an alternative embodiment, the hydrophobic membrane 150 may cover the lower matrix 130, or both the upper matrix 110 and the lower matrix 130. In the event that the hydrophobic membrane 150 covers the lower matrix 130, complimentary holes would be located in the wells 135 of the lower matrix 130.

Figure 2:
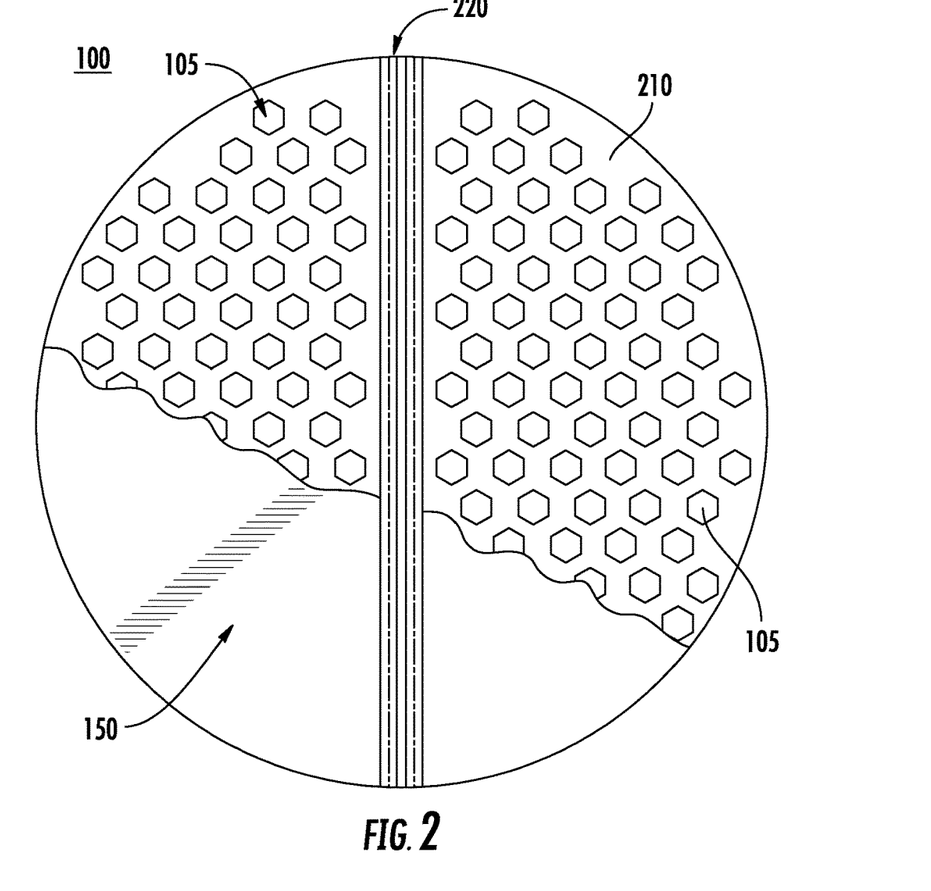
FIG. 2 is a top view of an example upper matrix.

FIG. 2 is a top view of the upper matrix 110. The upper matrix 110 may comprise polyurethane, rubber or silicone. FIG. 2 depicts a top view of the plurality of cells 105 in the upper matrix 110, which comprise openings in the top side 210 of the upper matrix 110. Although the cells 105 are shown as hexagonal in shape, the shape of the top of the cells 105 is illustrative, and those skilled in the art would understand that the cells 105 may be configured in any geometric shape that would properly accommodate the first reagent. The hydrophobic membrane 150 covers the entire top side 210 of the upper matrix 110. However, FIG. 2 does not show a portion of the hydrophobic membrane 150, for explanatory purposes. The hydrophobic membrane 150 is flexible and permits the gas that is generated to permeate through the hydrophobic membrane 150. The top side 210 of the upper matrix 110 may include at least one upper groove 220 to increase the pliability of the upper matrix 110. FIG. 2 depicts one upper groove 220 spanning the diameter of the upper matrix 110, although more than one grove may be utilized.

Figure 3:
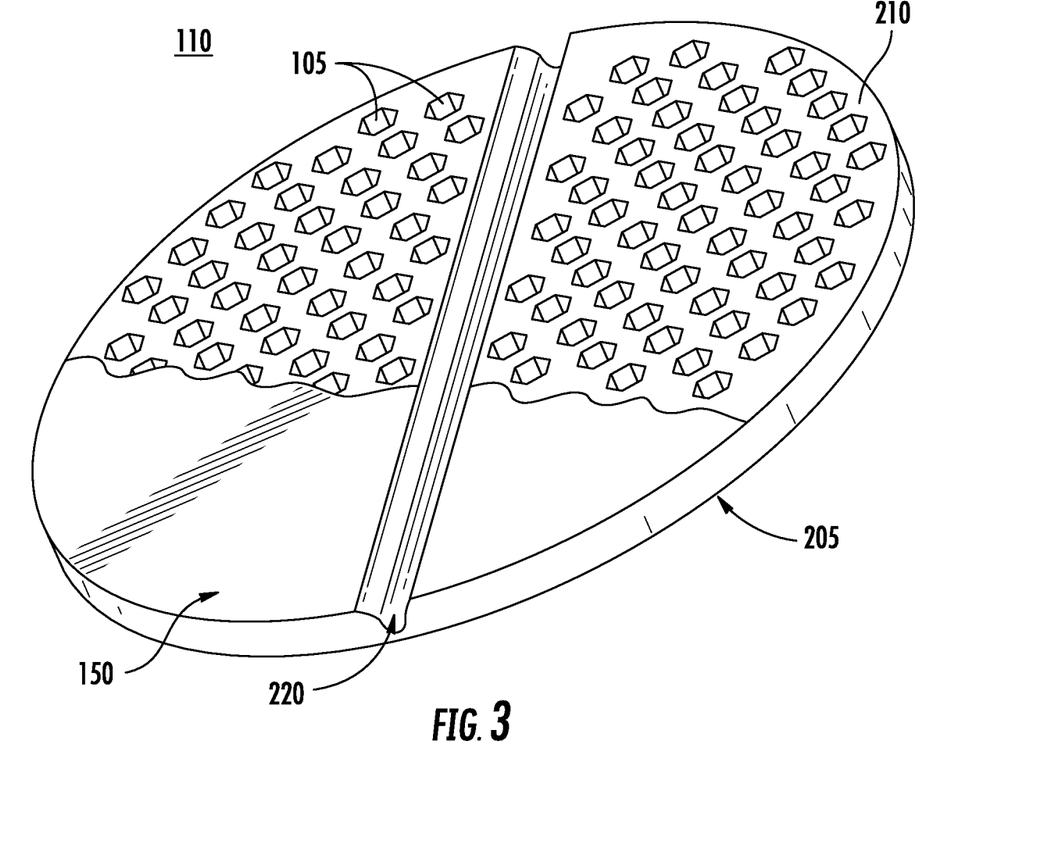
FIG. 3 is an isometric view of the top of the upper matrix.

FIG. 3 shows a perspective view of the top side 210 of the upper matrix 110 illustrating the tops of the cells 105 and the upper groove 220. In this figure, as with FIG. 2, a portion of the hydrophobic membrane 150 is not shown for simplicity.

Figure 4:
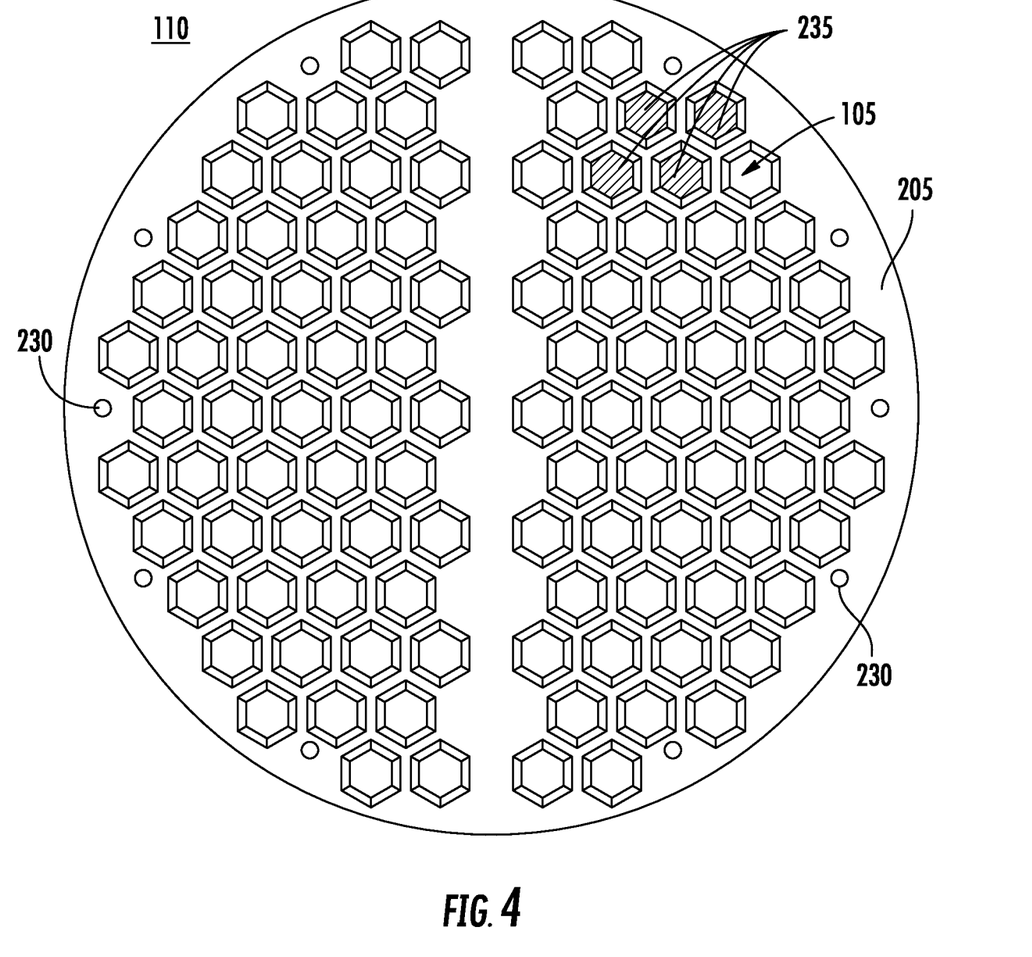
FIG. 4 is a bottom view of the upper matrix.

FIG. 4 shows the bottom side 205 of the upper matrix 110. The bottom side 205 is configured to be in contact with the middle layer 120. The cells 105 are shown as hexagonal in shape. However, as aforementioned, the shape of the cells 105 is illustrative and may be in any appropriate geometric shape. As illustrated in FIG. 4, the cells 105 may be arranged in a honeycomb pattern. The bottom side 205 of the upper matrix 110 may include a number of holes 230 configured to receive pegs from the lower matrix 130, in order to keep the upper matrix 110 and the lower matrix 130 properly aligned.

The cells 105 contain a first reagent 235. In one embodiment, the first reagent 235 by way of example is sodium bicarbonate. The first reagent 235 may fill a few cells 105 or a portion of the cells 105. However, it is most likely that most or all of the cells 105 contain the first reagent 235. In this embodiment, each cell may contain approximately 0.06g of sodium bicarbonate. However, more or less reagent, or a different reagent, may be utilized.

Figure 5:
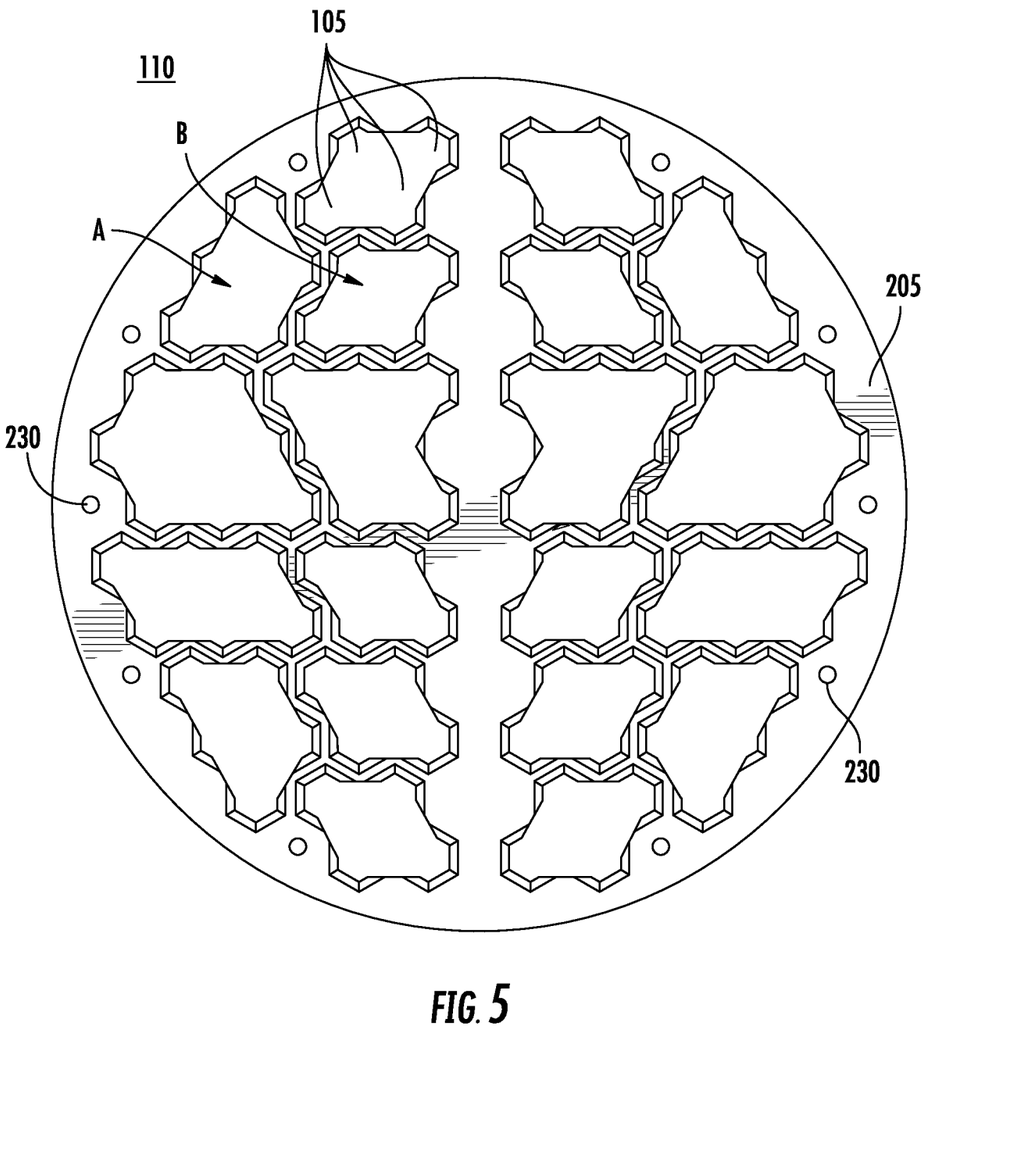
FIG. 5 is a bottom view of the upper matrix in an alternative embodiment.
Figure 6:
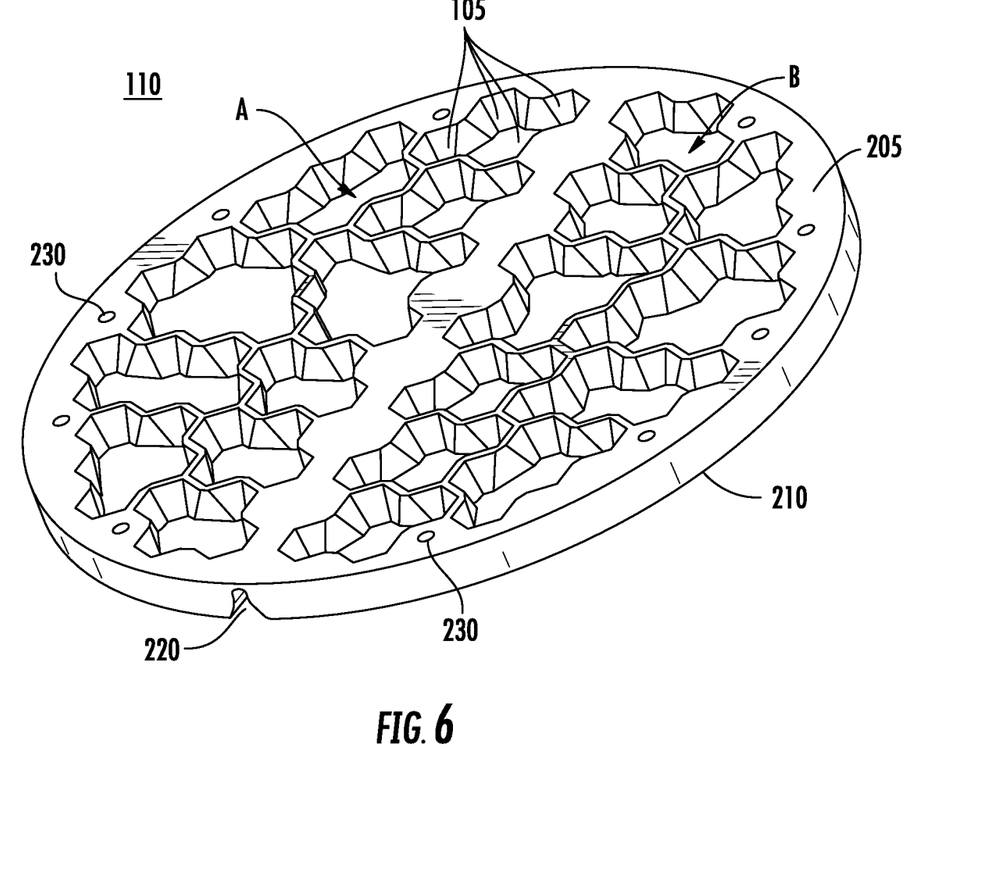
FIG. 6 is an isometric view showing the bottom of the upper matrix in the alternative embodiment.

FIG. 5 is an alternative embodiment of the upper matrix 110 whereby a plurality of cells 105 may be grouped together to form a larger cell, or a cell "cluster". As shown in FIG. 5, and also in the perspective view of FIG. 6, for example, cluster A is a 5 cell grouping and cluster B is a 4 cell grouping. Any size cell or grouping may be configured, depending upon the amount of gas desired to be generated at one time. The cells 105 may be the shape of an inverted funnel. The inverted funnel shape of the cells 105 optimizes the mixing of the first reagent and the second reagent. The purpose and process of the mixing of the reagents will be described in greater detail hereinafter.

Figure 7:
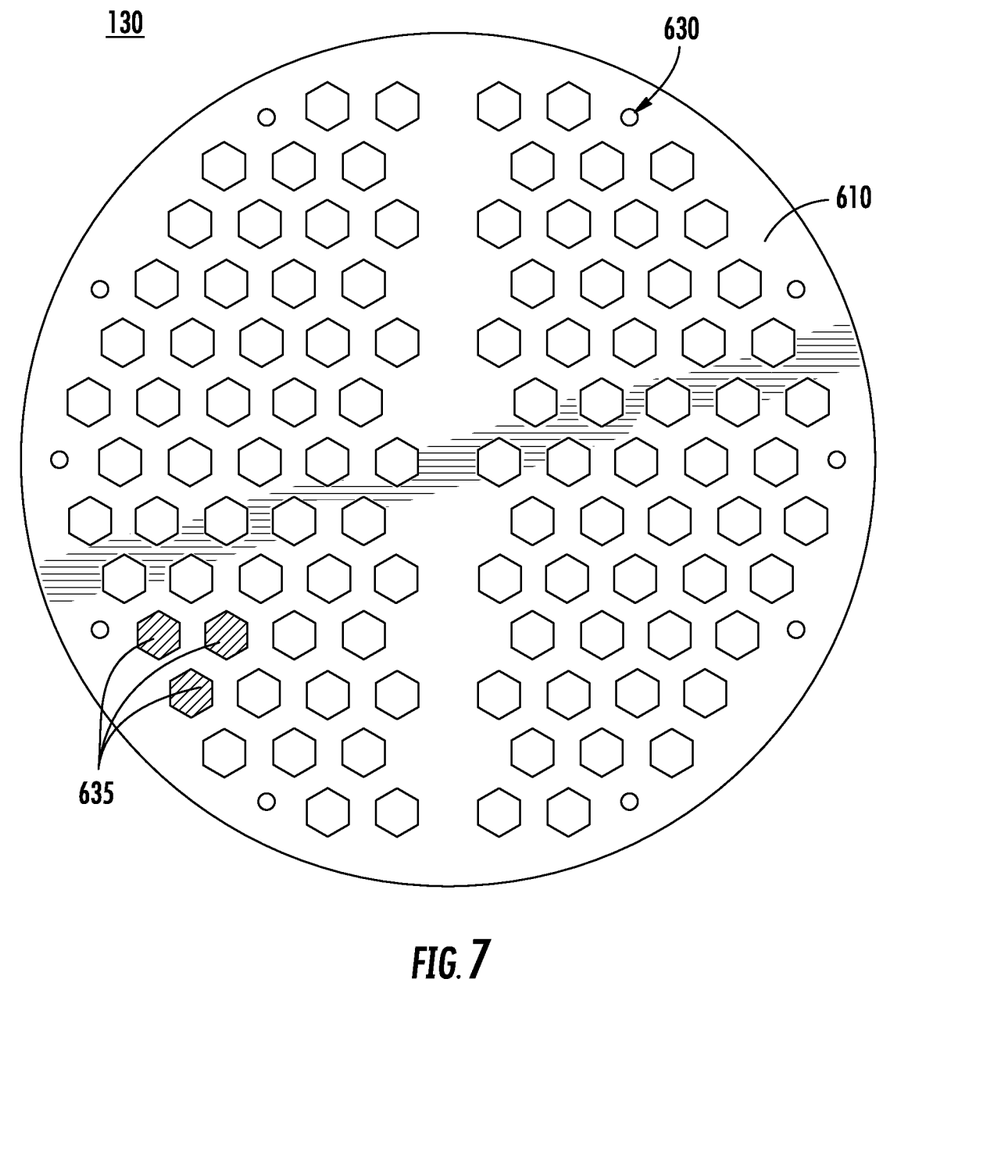
FIG. 7 is a top view of an example lower matrix.

FIG. 7 shows a top view of the lower matrix 130. The lower matrix 130 may comprise polyurethane, rubber or silicone. The top side 610 of the lower matrix 130 is configured to be in contact with the middle layer 120. The lower matrix 130 may include a number of pegs 630 that are complimentary to, and insert into, the holes 230 of the upper matrix 110. The hole 230 and peg 630 configuration is an optional means of coupling the upper matrix 110, lower matrix 130, and middle layer 120 together and also the membrane. The arrangement of the wells 135 in the lower matrix 130 should optimally match the configuration of the cells 105 in the upper matrix 110. The perimeter of each well 135 preferably aligns with the perimeter of a cell 105 in the upper matrix 110, although exact alignment is not required.

As an example, FIG. 7 shows single wells 135 that align with the single cells 105 depicted in FIG. 4. Typically, all wells 135 contain the second reagent 635, which may be at least 70% acetic acid depending upon the volume of the wells. However, more or less reagent, or a different reagent, may be utilized. Although the second reagent 635 is graphically illustrated as filling only a few wells 135, it is most likely that most or all of the wells 135 contain the second reagent 635.

As explained in a process described hereinafter, when one or more openings in the middle layer 120 are formed, the first reagent 235 in the cells 105 passes through openings in the middle layer 120 and mixes with the second reagent 635 in the wells 135. The reagents 235, 635 mix and react to generate a gas.

In one embodiment, the first reagent 235 is sodium bicarbonate and the second reagent 635 is acetic acid, wherein the reaction produces carbon dioxide. Each cell 105 and well 135 may contain enough materials to produce 15 cc of carbon dioxide.

Figure 8:
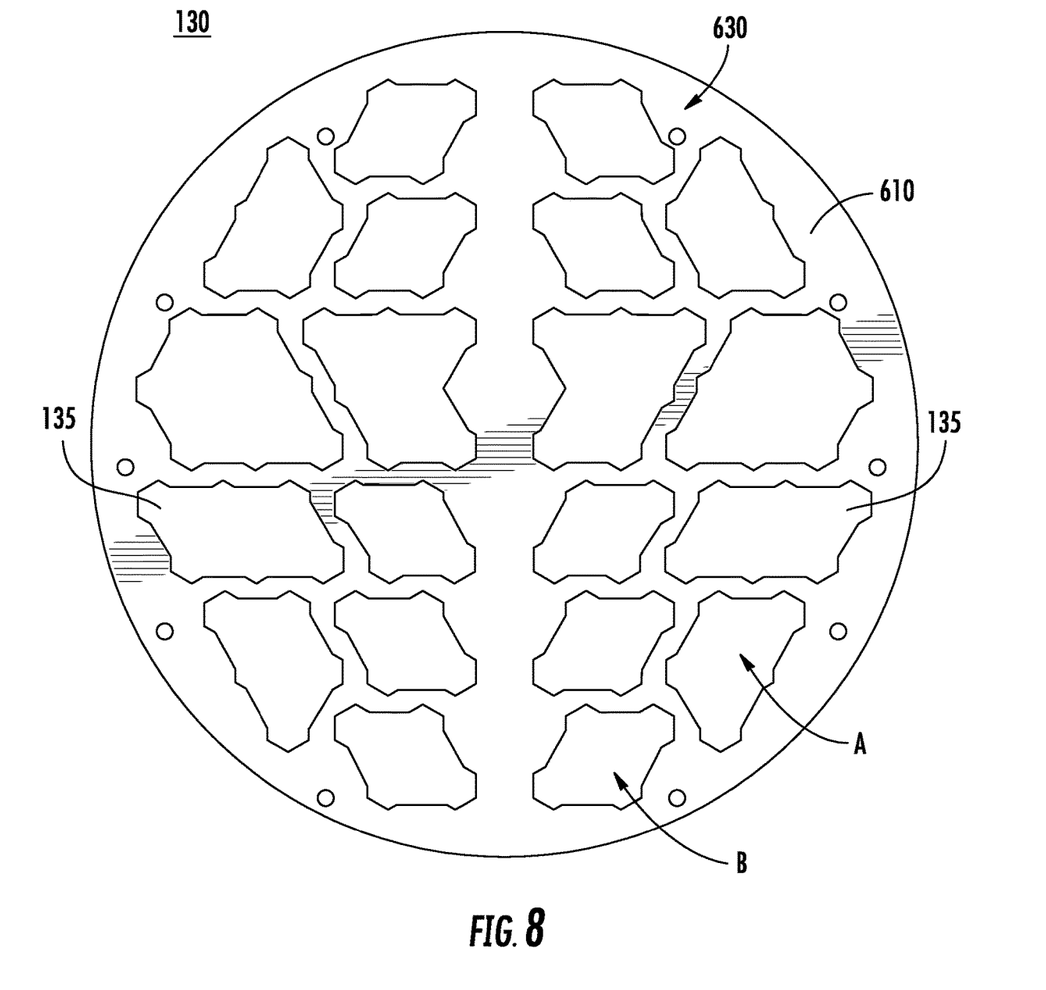
FIG. 8 is a top view of the lower matrix in an alternative embodiment.

FIG. 8 is a top view of the lower matrix 130 in an alternative embodiment. This embodiment includes one or more groupings of wells 135, comprising a plurality of wells 135 joined together to form a well "cluster." Alternatively, these wells 135 may simply comprise a larger-sized well 135. As with the embodiment shown in FIG. 7, each well 135 cluster is configured to be generally aligned with a complimentary cell 105 in the upper matrix 110. Accordingly, the embodiment of the lower matrix 130 shown in FIG. 8 would be complimentary with the embodiment of the upper matrix 110 shown in FIG. 5. As such, the perimeter of each well 135 may be configured to overlap the same area as a cluster of cells 105 in the upper matrix 110. Well A is an example of a well 135 configured to accommodate a 5 cell 105 cluster, and Well B is an example of a well 135 configured to accommodate a 4 cell 105 cluster.

Figure 9:
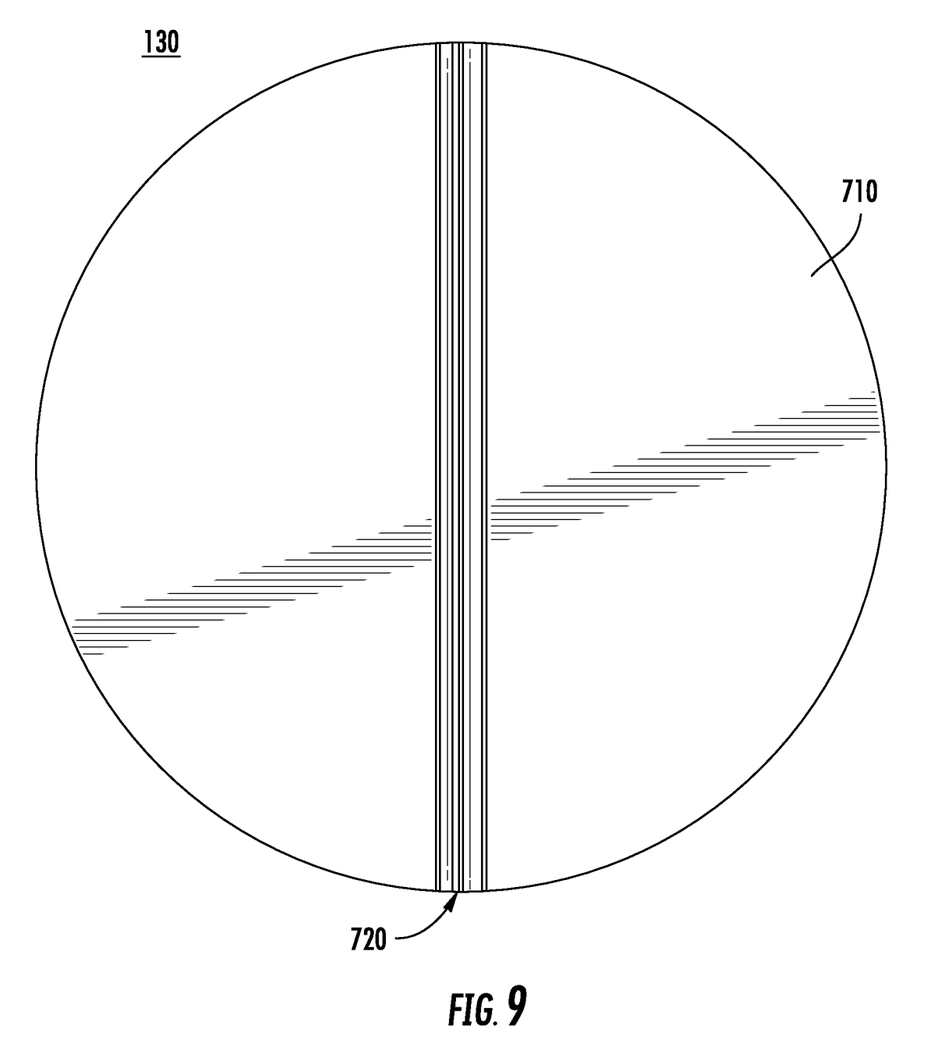
FIG. 9 is a bottom view of the lower matrix.

FIG. 9 is a bottom view of the lower matrix 130. The bottom side 710 comprises a surface which encloses the wells 135 and contains the second reagent 635 within the wells 135. The bottom side 710 may comprise at least one lower groove 720 that spans the diameter of the lower matrix 130 to increase the pliability of the lower matrix 130, and is complimentary to the upper grove 220.

Figure 10:
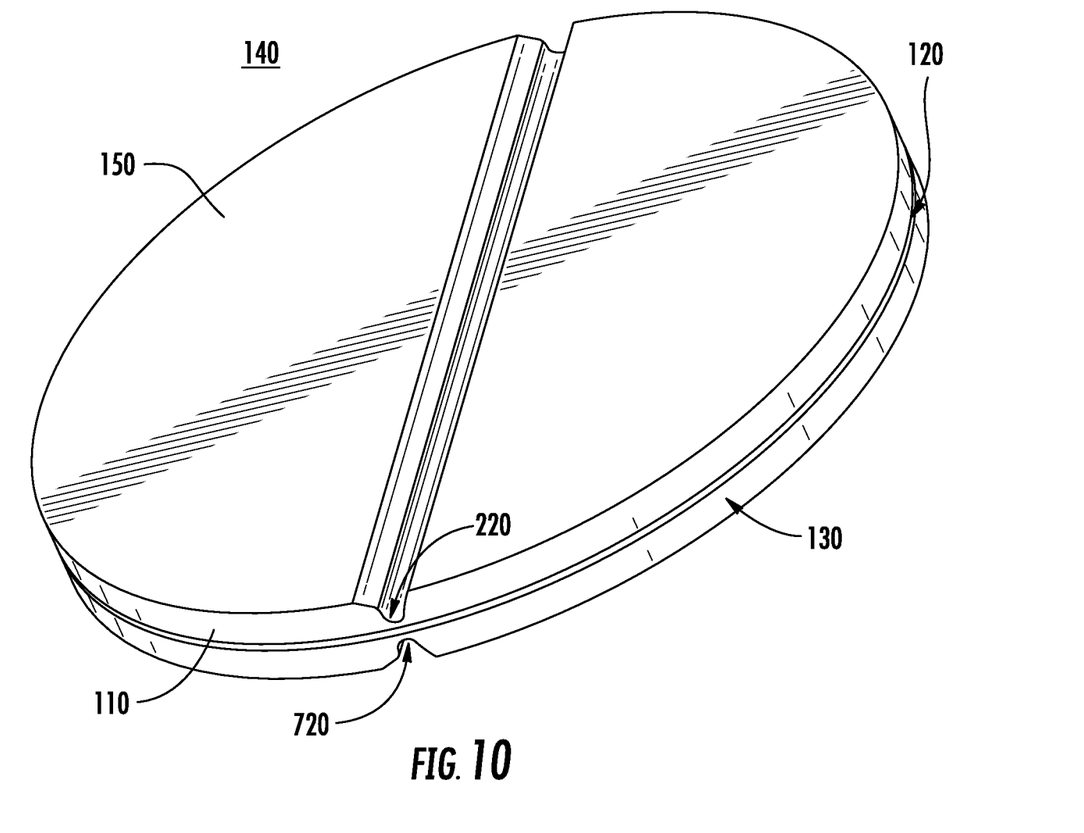
FIG. 10 is an isometric view of the multi-layer structure comprising the upper matrix, lower matrix, and middle layer.

FIG. 10 is an isometric view of the multi-layer structure 140 comprising the hydrophobic membrane 150, the upper matrix 110, the lower matrix 130, and the middle layer 120. As shown in FIG. 10, the upper matrix 110 includes at least one upper groove 220, and the lower matrix 130 includes at least one complimentary matching lower groove 720. The at least one upper groove 220 in the upper matrix 110 and the at least one lower groove 720 in the lower matrix 130 increase the pliability of the multi-layer structure 140 and allows the multi-layer structure 140 to fold. Advantageously, these grooves 220, 720 may provide the physician with the option to bend the expandable breast implant to create an easier insertion process and to allow a small incision. Although only one upper groove 220 on the upper matrix 110 and one lower groove 720 on the lower matrix 130 are shown, it should be understood that the upper matrix 110 and lower matrix 130 may have multiple grooves to allow the expandable breast implant 100 to fold at multiple locations.

Figure 11:
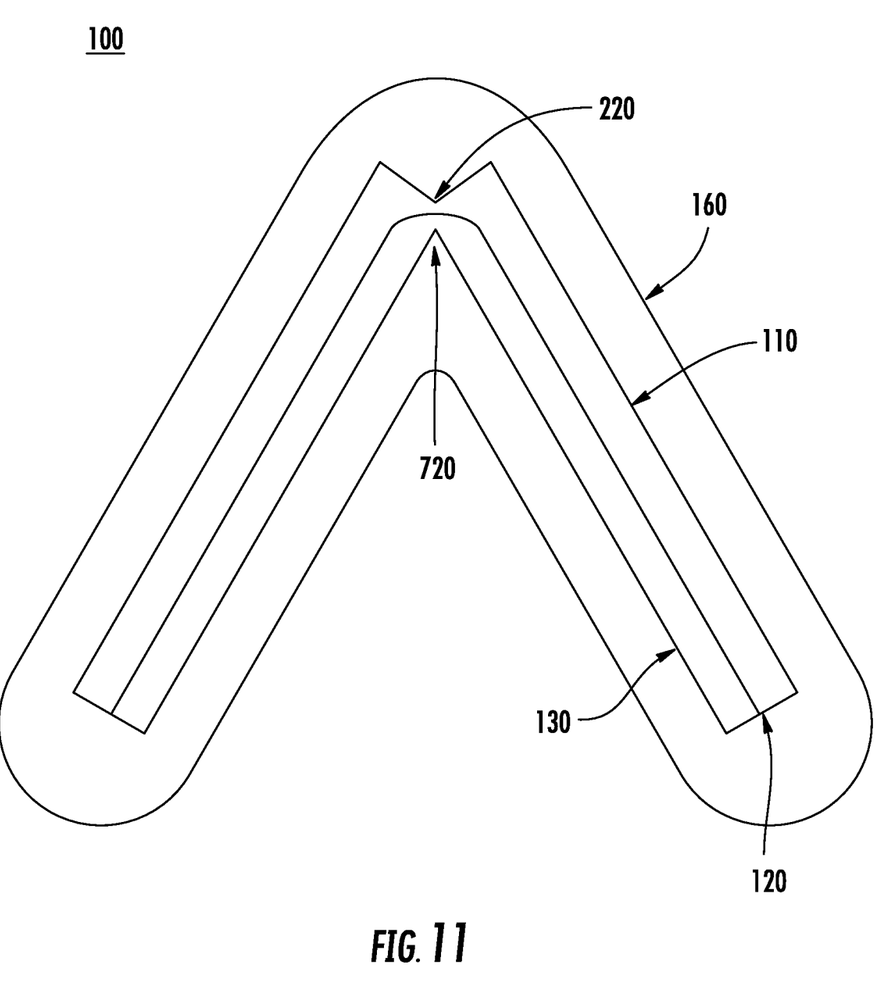
FIG. 11 is an example cross-sectional view of a folded expandable breast implant.

FIG. 11 is a cross-sectional view of a folded expandable breast implant 100. The expandable breast implant 100 may fold at the location of the upper and lower grooves 220, 720 in the upper matrix 110 and lower matrix 130, respectively. FIG. 11 depicts one upper groove 220 in the upper matrix 110 and one lower groove 720 in the lower matrix 130.

Figure 12:
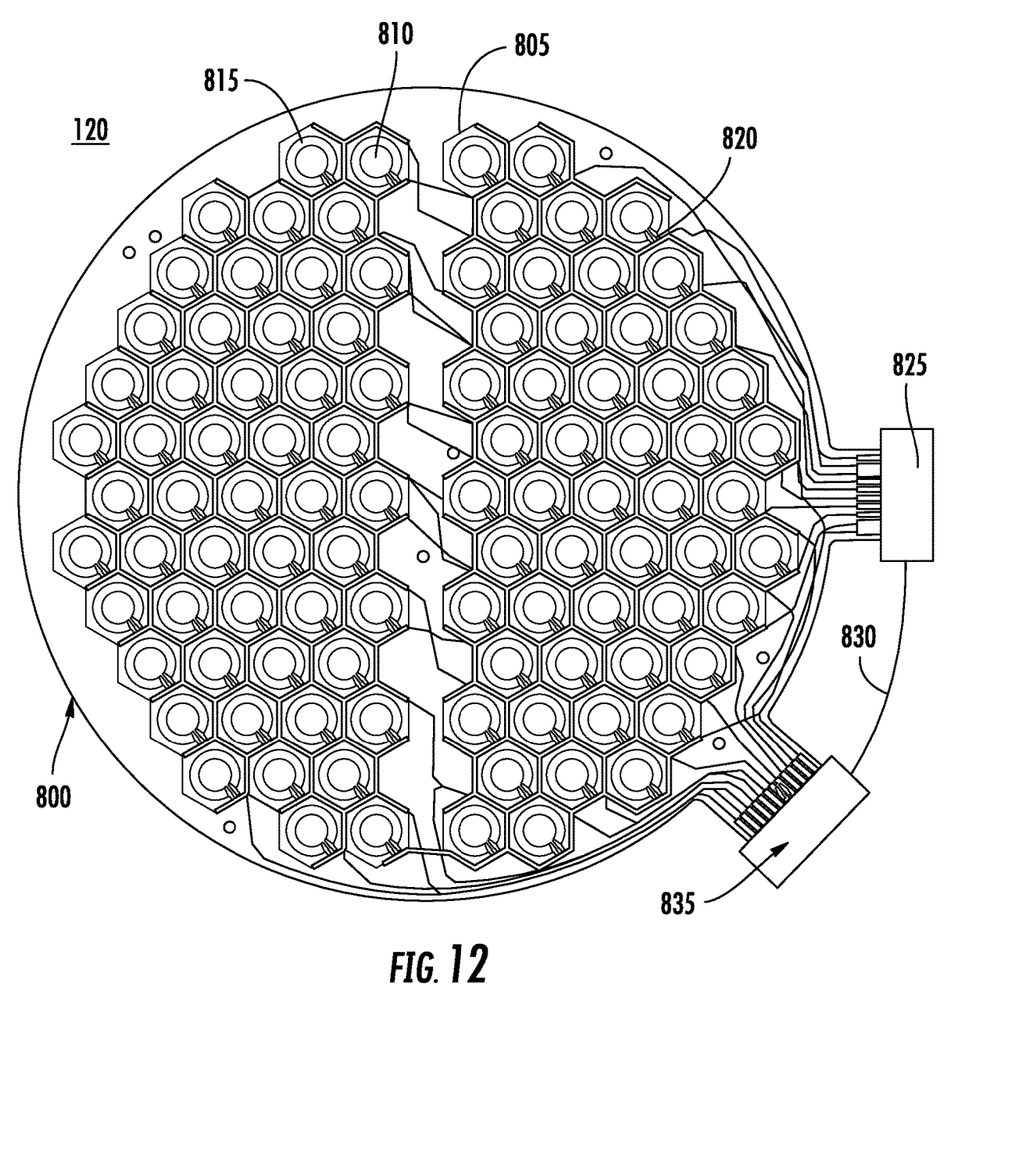
FIG. 12 is a plan view of an example middle layer comprising a flex printed circuit ("FPC")

FIG. 12 is a plan view of an example middle layer 120. The middle layer 120 comprises a flexible circuit "board." In one embodiment, the flexible circuit board is a printed circuit on thin, flexible film 800 (hereinafter "flex printed circuit" or "FPC") as depicted in FIG. 12. In one embodiment, the FPC 800 is polyurethane. The FPC 800 comprises a plurality of cells 805. Each cell 805 may be hexagonally shaped. The configuration of the cells 805 in the FPC 800 should generally align with the cells 105 in the upper matrix 110 and the wells 135 in the lower matrix 130. Accordingly, the shape of the cells 805 is illustrative, and the cells 805 may be constructed in any geometric shape that is complimentary to the cells 105 and the wells 135. The cells 805 may be arranged in a honeycomb structure as shown in FIG. 12. Each cell 805 comprises a resistor 815, conductors 820, and an area of thin film 810. FIG. 12 depicts a circular resistor 815. The conductors 820 terminate at a first end at the resistor 815, and at a second end at a power bus 825. The power bus 825 is electrically coupled via a conductor 830 to the control system 835.

Although the circuit may be printed on the polyurethane sheet as shown, the circuit may be coupled to the polyurethane sheet by glue heat or another appropriate manner.

Figure 13:
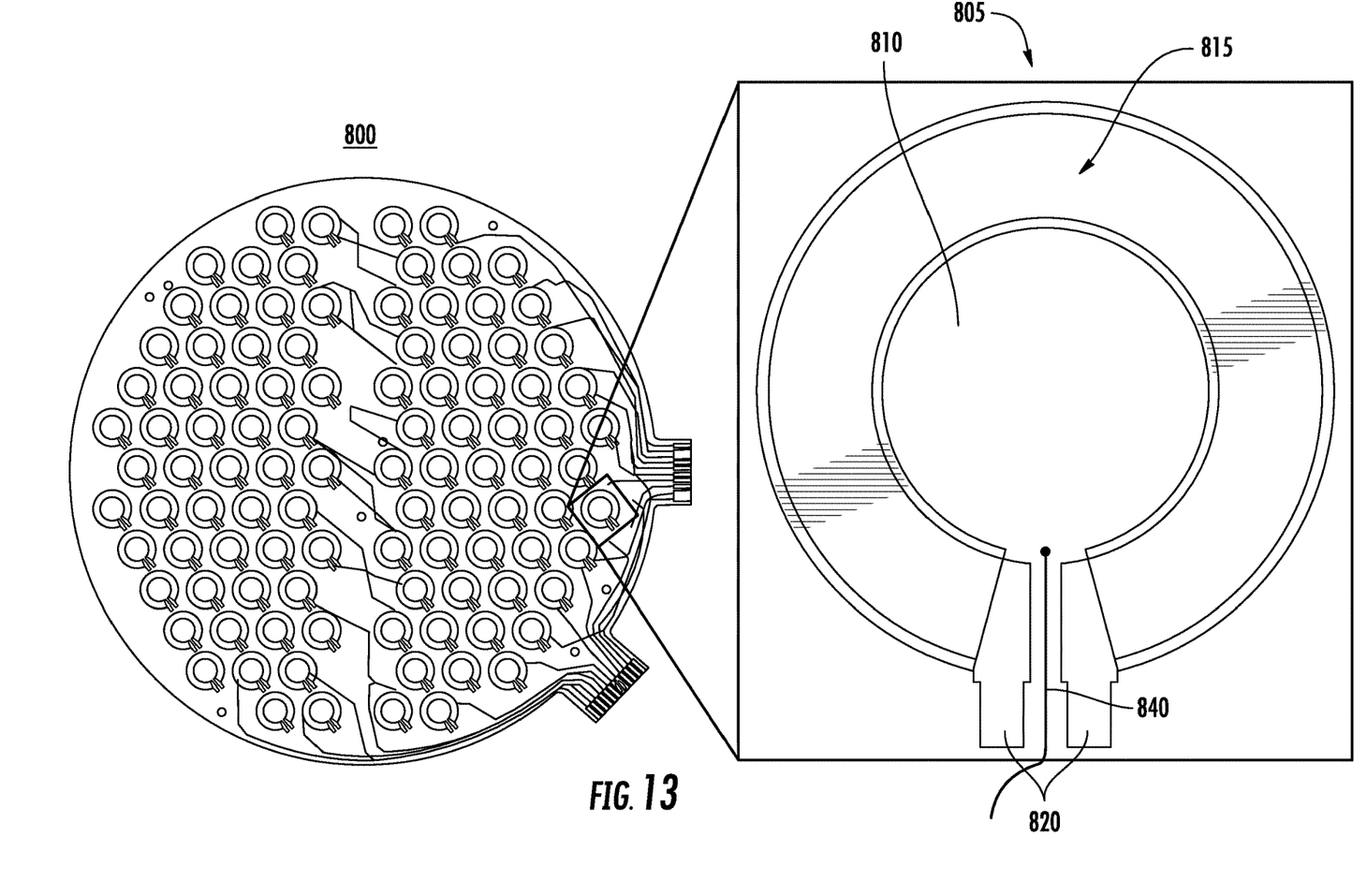
FIG. 13 is a top view of a FPC showing a magnified view of a cell in the FPC.

FIG. 13 shows a top view of a FPC 800 and a magnified view of a single cell 805 in the FPC 800. The magnified view of a cell 805 shows a resistor 815, conductors 820, and an area of thin film 810 substantially surrounded by the circular resistor 815.

In an alternative embodiment, the cell 805 may also include a sensor 840. The sensor 840, which is coupled to the control system 835 by one or more conductors (not shown) may comprise a pressure sensor or chemical sensor, and detects whether the reagents have mixed and reacted successfully. Alternatively, the sensor 840 may comprise any sensor that one skilled in the art would understand would detect successful completion of the reaction. Although the sensor 840 is shown in FIG. 13 as integral to each cell 805, one or more sensors 840 may be utilized for the entire implant.

As will be explained in greater detail hereinafter, as current is applied to the conductors 820, it flows through the resistor 815, thereby energizing and heating the resistor 815. In one embodiment, the resistor 815 receives 1 W of electric power. When the resistor 815 achieves the melting temperature of the FPC 800, the FPC 800 melts and ruptures, thereby allowing the first and second reagents 235, 635 to mix together and generate the gas. In one embodiment, each resistor 815 may have a resistivity of approximately 123 ohms and heat to a temperature of approximately 120° C. Because the melting temperature of the FPC 800 is lower than 120° C., the area of thin film 810 will melt and rupture as each resistor 815 achieves a temperature of approximately 120° C.

Figure 14A:
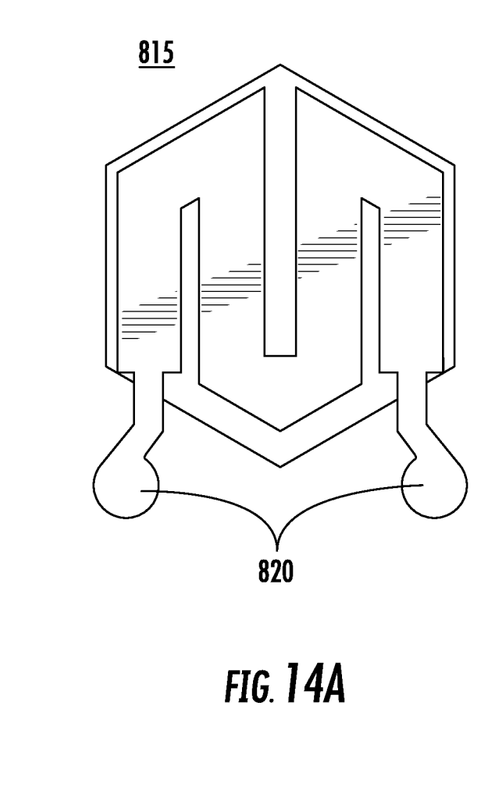
FIG. 14A is a top view of a resistor.
Figure 14B:
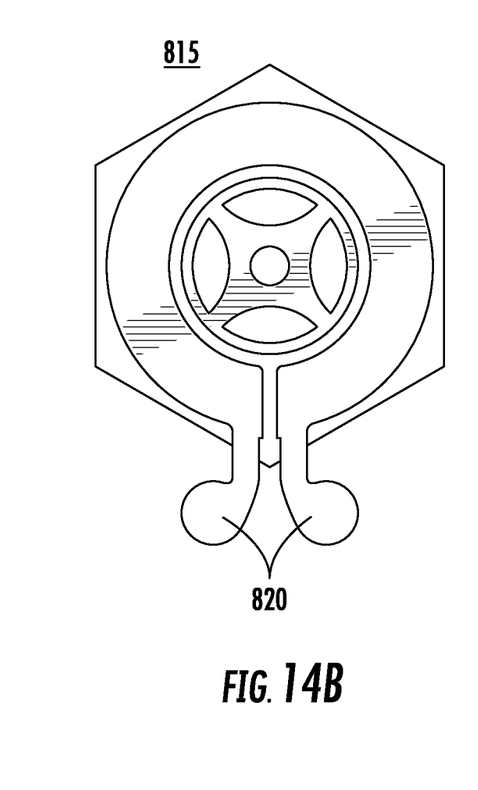
FIG. 14B is a top view of a resistor in an alternative embodiment.
Figure 14C:
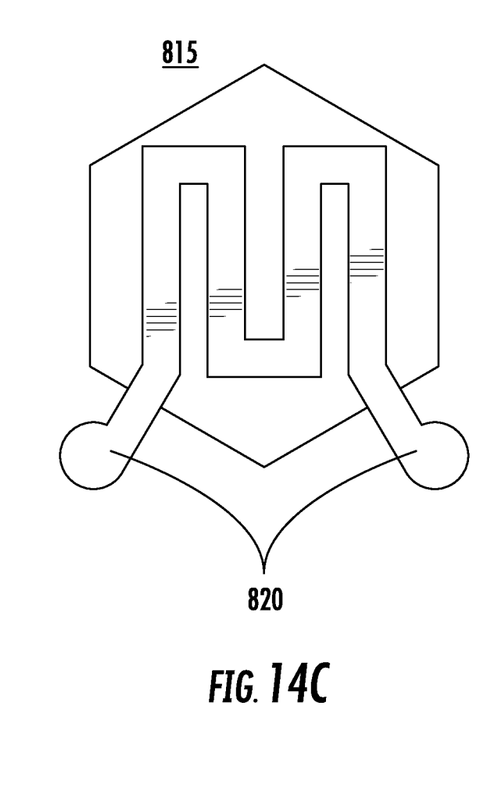
FIG. 14C is a top view of a resistor in another alternative embodiment.

The resistors 815 in FIGS. 12 and 13 are shown to have a circular design. However, the design of the resistors 815 may be in any shape. FIG. 14A, 14B, and 14C are diagrams of top views of example resistors 815. FIG. 14A, 14B, and 14C illustrate alternative designs of the resistors 815.

Figure 15:
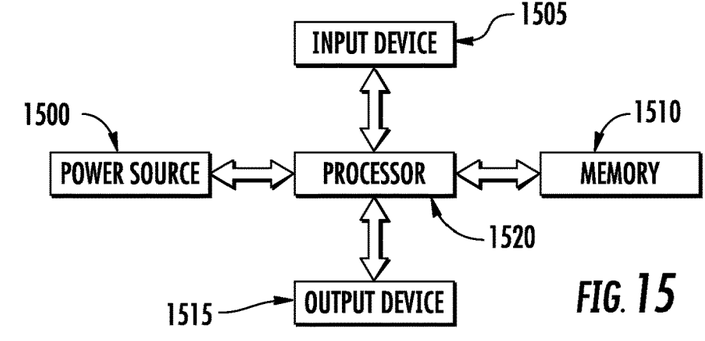
FIG. 15 is a block diagram of a control system that is electrically coupled to the FPC.

FIG. 15 is a block diagram of a control system 835 in which one or more features of the disclosure may be implemented. The control system 835 includes a power source 1500, one or more input devices 1505, a memory 1510, one or more output devices 1515, and a processor 1520. It should be understood that the control system 835 may include additional components not shown in FIG. 15.

The power source 1500 supplies power to the control system 835. The power source 1500 may include, but is not limited to, a battery or an inductive power receiver, which receives power through an inductive power generator (not shown) external to the implant 100.

The input devices 1505 may include an antenna or other wireless network connection (e.g., any wireless interface for transmission and/or reception of wireless signals). In one embodiment, the processor 1520 receives and transmits information via radio frequency (RF) communication such as Bluetooth, near field communication (NFC), or Wi-Fi. In one embodiment, the input devices 1505 may include signals from sensors 840 in the cells 805 to indicate whether a chemical process, explained in FIG. 16 hereinafter, has been successfully completed.

The memory 1510 may include a volatile or non-volatile memory, for example, random access memory (RAM), dynamic RAM, or a cache. The memory 1510 stores information which may include the unique address of each cell 805.

The output devices 1515 include one or more current drivers that are coupled to the conductors 820 of selected cells 805. These current drivers may apply current to the appropriate conductors 820 to activate a desired resistor 815.

The processor 1520 is configured to receive a signal via an input device 1505. The processor 1520 determines the appropriate action to take, which may include selection of one more resistors 815 and ultimately energizing those resistors. As such, the processor 1520 selectively activates the appropriate resistor 815 of the desired cell 805.

Figure 16:
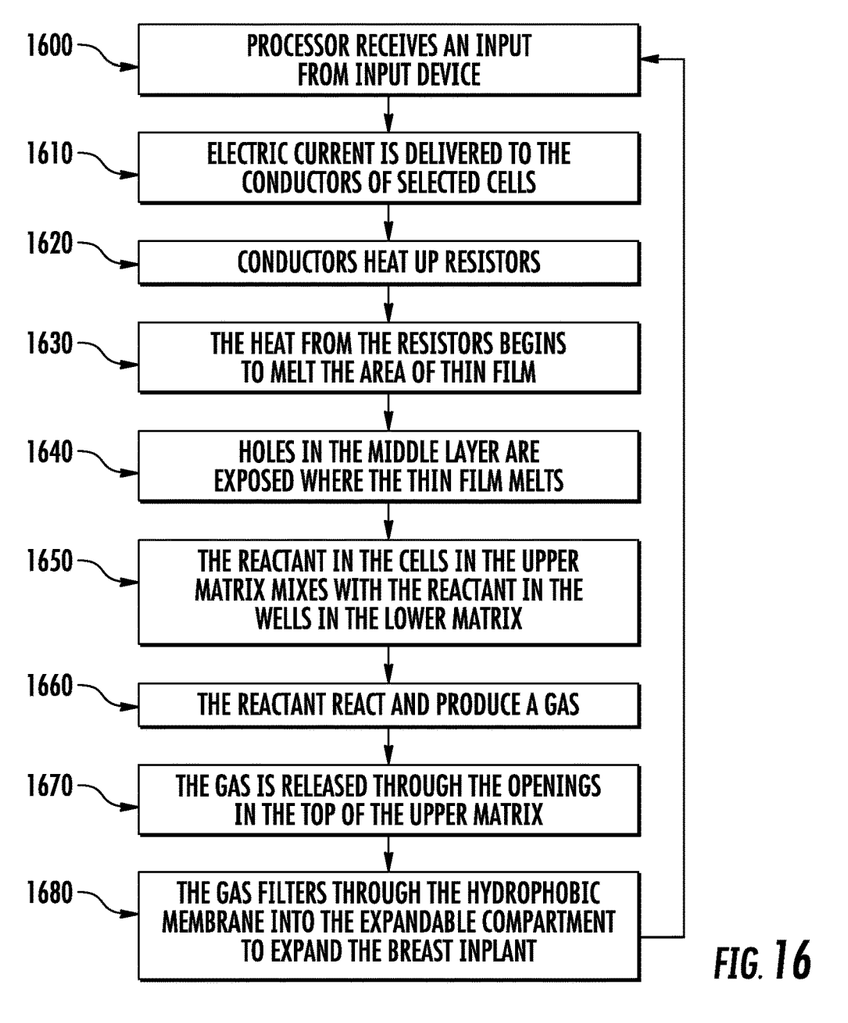
FIG. 16 is a flow diagram of a procedure which is used in conjunction with the disclosed embodiments.

FIG. 16 is a flow diagram of a process for expanding the breast implant 100. The process is initiated (step 1600) when the processor 1520 wirelessly receives an input from an input device 1505. Typically, the input comprises an instruction to activate one or more cells 805. If necessary, the processor 1520 "translates" the instruction into one or more addresses of one or more cells 805. Once the processor 1520 determines which cell 805 to activate, the output device 1515 drives current to the selected cell 805. Therefore, current is delivered to conductors 820 of the selected cell 805 (step 1610). The conductors 820 energize one or more resistors 815 (step 1620). As the selected resistor 815 heats up, the area of thin film 810 substantially surrounded by the heated resistor 815 melts (step 1630). As the area of thin film 810 melts, holes are introduced in the middle layer 120 (step 1640) allowing the first reagent 235 in the cells 105 from the upper matrix 110 to mix with the second reagent 635 in the wells 135 of the lower matrix 130 (step 1650). The mixed reagents 235, 635 react and release a gas (step 1660). The gas produced by the reaction is released through the openings in the top of the upper matrix 110 (step 1670). The released gas may permeate through the hydrophobic membrane 150 into the expandable shell 160 to expand the implant 100 (step 1680).

It should be understood that there may be different configurations of the implant once the gas is generated. In a first embodiment, the implant 100 may be filled with silicone, whereby the gas permeates throughout the silicone and inflates the expandable shell 160. In a second embodiment, the implant 100 is empty and only fills the expandable shell 160. In yet another embodiment, the implant 100 may include a plurality of separate compartments, and the gas inflates the plurality of separate compartments. Those of skill in that art would understand that other embodiments would be possible in accordance with the teachings herein.

This process may be repeated in accordance with a physician's care plan to expand the implant 100 to the desired size. The expandable breast implant 100 may be configured to limit the number of repetitions per hour and/or per day to avoid overexpansion of the expandable breast implant 100. In this manner, the processor 1520 may provide a limit on the number of resistors 815 that are activated within a certain amount of time. Additionally, the processor 1520 may be pre-programmed to activate the resistors 815 in a certain sequence, which may be automatically implemented with any intervention by the physician or the patient.

In yet another embodiment, the processor 1520 may wirelessly communicate the measurements taken by the one or more sensors 840 to a network (not shown), for ultimate reception by a physician. In this matter, a physician may remotely monitor the course of treatment (i.e. expansion) if the expansion process is self-administered or administered automatically via a pre-programmed sequence. As one optional safety precaution, if the sensor 840 comprises a pressure sensor, once the total pressure of the expandable implant reaches a predetermined level, power to the resistors 815 is removed, and alternatively permanently disconnected.

At least one advantage of this expandable breast implant 100 is that the patient may expand the size of the implant 100 without additional surgeries or invasive procedures. In addition, it is possible to avoid the issues that arise at high elevations as experienced in breast implants that contain pressurized carbon dioxide cartridges.

What is claimed is:

1. An expandable implant comprising:
    a flexible shell, enclosing:
        an upper matrix having a plurality of cells, each cell including a first reagent;
        a lower matrix having a plurality of wells, each well being at least partially aligned with one of said cells, and each well including a second reagent; and
        a middle layer between the upper matrix and the lower matrix, having at least one selectively activateable membrane, each said at least one membrane being located between a cell and its aligned well;
    a controller, for activating at least one of said at least one membranes, and permitting the first reagent to mix with said second reagent to produce a gas, and expand said flexible shell.

2. The expandable implant of claim 1, further comprising hydrophobic membrane.

3. The expandable implant of claim 2, wherein each of the plurality of cells are arranged in a honeycomb structure.

4. The expandable implant of claim 2, wherein each of said at least one membrane includes a resistor, and current that is applied to the resistor activates the said at least one membrane .

5. The expandable implant of claim 2, wherein a plurality of cells comprise a cell cluster.

6. The expandable implant of claim 4 further comprising a controller, which selectively applies current to the resistors.

7. The expandable implant of claim 2, wherein each of the plurality of cells contains sodium bicarbonate.

8. The expandable implant of claim 1, further comprising at least one sensor, for determining whether said gas has been produced.

9. The expandable implant of claim 1, wherein the middle layer comprises a flex printed circuit.

10. The expandable implant of claim 9, wherein the flex printed circuit includes a plurality of resistors.

11. The expandable implant of claim 10, wherein each of the plurality of resistors are selectively activatable.

12. The expandable implant of claim 1, wherein the middle layer comprises a layer of polyurethane coupled to a flex printed circuit.

13. The expandable implant of claim 1, wherein each of the plurality of wells include ascetic acid.

14. The expandable implant of claim 1, wherein the controller automatically activates a plurality of said membranes in a predetermined sequence.

15. A method for expanding a breast implant comprising:
    providing a flexible shell, enclosing:
        an upper matrix having a plurality of cells, each cell including a first reagent;
        a lower matrix having a plurality of wells, each well-being at least partially aligned with one of said cells, and each well including a second reagent; and
        a middle layer between the upper matrix and the lower matrix, having a plurality of selectively activatable membranes, each membrane being located between a cell and its aligned well;
    activating one of said membranes, and permitting the first reagent to mix with said second reagent to produce a gas, to expand said flexible shell.

16. The method for expanding a breast implant of claim 15, wherein the controller is programmed to automatically activate a plurality of said membranes.

17. The method for expanding a breast implant of claim 16, wherein the automatic activation comprises a predetermined sequence on a predetermined schedule.

18. The method for expanding a breast implant of claim 17, further comprising utilizing at least one sensor to confirm whether said gas has been produced.

19. The method for expanding a breast implant of claim 18, further comprising wirelessly transmitting sensor data to a physician.

20. The method for expanding a breast implant of claim 16, further comprising the controller wirelessly programmed by a physician.

* * * * *

UNITED STATES PATENT AND TRADEMARK OFFICE
CERTIFICATE OF CORRECTION

PATENT NO. : 10,660,742 B2
APPLICATION NO. : 15/983035
DATED : May 26, 2020
INVENTOR(S) : Yehuda Algawi et al.

It is certified that error appears in the above-identified patent and that said Letters Patent is hereby corrected as shown below:

In the Specification
In Column 2, Line 38, delete "shell 160" and insert -- expandable shell 160 --, therefor.
In Column 4, Line 17, delete "biocarbonate" and insert -- bicarbonate --, therefor.

In the Claims
In Column 7, Line 50, in Claim 4, delete "membrane ." and insert -- membrane. --, therefor.

Signed and Sealed this
Twenty-fourth Day of January, 2023

Katherine Kelly Vidal
*Director of the United States Patent and Trademark Office*